(12) United States Patent
Dowd

(10) Patent No.: US 7,293,451 B2
(45) Date of Patent: Nov. 13, 2007

(54) SHARPNESS TESTER

(76) Inventor: Peter Christopher Dowd, 7 Sussex Street, Hamilton (NZ)

( * ) Notice: Subject to any disclaimer, the term of this patent is extended or adjusted under 35 U.S.C. 154(b) by 257 days.

(21) Appl. No.: 11/075,761

(22) Filed: Mar. 10, 2005

(65) Prior Publication Data

US 2006/0201237 A1 Sep. 14, 2006

(51) Int. Cl.
*G01B 5/28* (2006.01)

(52) U.S. Cl. ...................................................... 73/105

(58) Field of Classification Search ............. 83/522.27; 73/104, 105
See application file for complete search history.

(56) References Cited

U.S. PATENT DOCUMENTS

| 4,528,843 A | * | 7/1985 | Juranitch | ..................... 73/104 |
| 5,059,483 A | * | 10/1991 | Lunk et al. | ................. 428/383 |
| 5,571,956 A | * | 11/1996 | Sargent | ...................... 73/104 |

* cited by examiner

*Primary Examiner*—Robert Raevis
(74) *Attorney, Agent, or Firm*—Young & Thompson

(57) ABSTRACT

A sharpness tester for testing the sharpness of a blade. The tester has a blade holder 19 and a mounting arrangement 21, 22 for mounting a cuttable material 20. The blade holder 19 is mounted by a carriage 18 which is moveable on a track 14 so that the blade can move relative to the material 20 and contact the material. A linear distance measuring device and a force measuring device 21 enable the tester to determine the force required by part of the blade B to cut the material 20.

14 Claims, 6 Drawing Sheets

SHARPNESS TESTER

BACKGROUND OF THE INVENTION

This invention relates a sharpness tester.

It is often desirable to be able to measure the cutting ability of a cutting edge such as that of a blade e.g. a butcher's or meat processor's knife. Currently there is no known method of directly, accurately, reliably, repeatably and non-destructively measuring the cutting ability of a blade. Current methods are either subjective and/or measure ability of a blade to retain its edge. These methods do not provide the ability to accurately locate blunt/sharp portions of a blade.

SUMMARY OF THE INVENTION

The object of the present invention is to provide a sharpness tester whereby an objective and quantifiable test of the sharpness of a blade along multiple parts of the blade can be achieved and in manner, which ensures damage to the edge, is minimal.

Broadly according to one aspect the present invention provides a sharpness tester including a blade holder, a mounting arrangement for mounting of a cuttable material, a moving mechanism to cause relative movement between the blade holder and the mounting arrangement, and hence material when mounted by the mounting arrangement, whereby during such relative movement different parts of a blade held by the blade holder will cuttingly contact the material, the sharpness tester further including force meaning device and a location measurement device both operable, in use, to determine the force required by a part of the blade to cut the material.

According to one form of the invention, the blade holder is carried by a carriage, which is moveable by the moving mechanism relative to the mounting arrangement. The carriage can be moveably mounted on a track, which is inclined relative to the plane of material to be cut when the material is retained by the mounting arrangement. The track can be a pair of parallel track members.

The moving means can be a means for enabling controlled linear motion. For example, an electrically, hydraulically, pneumatically powered linear actuator. The location measurement means can be a linear distance measurement device operable to generate a signal representative of the position of the blade holder relative to the mounting arrangement.

According a preferred form of the invention, the force measurement means is a force measuring device forming part of the mounting arrangement. A microprocessor programmed to generate a profile of the force needed to cut material, mounted by the mounting arrangement, at points along the length of the blade can form part of the sharpness tester and derive the profile from signals received from the linear distance measurement device and the force measuring device.

According to a preferred form of the invention there is further provided puncturing means to puncture material, mounted by the mounting arrangement, prior to engagement of the material by a leading part of the blade.

Broadly according to a second aspect the invention provides a sharpness tester including a moveable blade holder, a mounting arrangement for mounting of a cuttable material, a moving mechanism to cause relative movement between the blade holder and the mounting arrangement whereby, relative to a plane in which material is mounted by the mounting arrangement, the blade progressively moves simultaneously through and along the material, the sharpness tester further including a force measuring device and a location measurement device to determine the force required by a part of a blade to cut the material.

Preferably the mounting arrangement is such as to retain the material in a vertical orientation, an upper end of the material being coupled to the force measurement means.

Preferably the blade holder is moveable along a downwardly inclined track, the track being disposed such that a lower part thereof is adjacent the material when mounted by the mounting arrangement.

Preferably the sharpness tester includes a microprocessor which derives information from the force measurement means and the location measurement means and is programmed to generate a profile of the force needed to cut the material, held by the mounting arrangement, at points along the length of the blade at which readings have been taken.

BRIEF DESCRIPTION OF THE DRAWINGS

In the following more detailed description of the invention according to one preferred embodiment reference will be made to the accompanying drawings in which:—

DETAILED DESCRIPTION OF A PREFERRED EMBODIMENT

Figure 1:
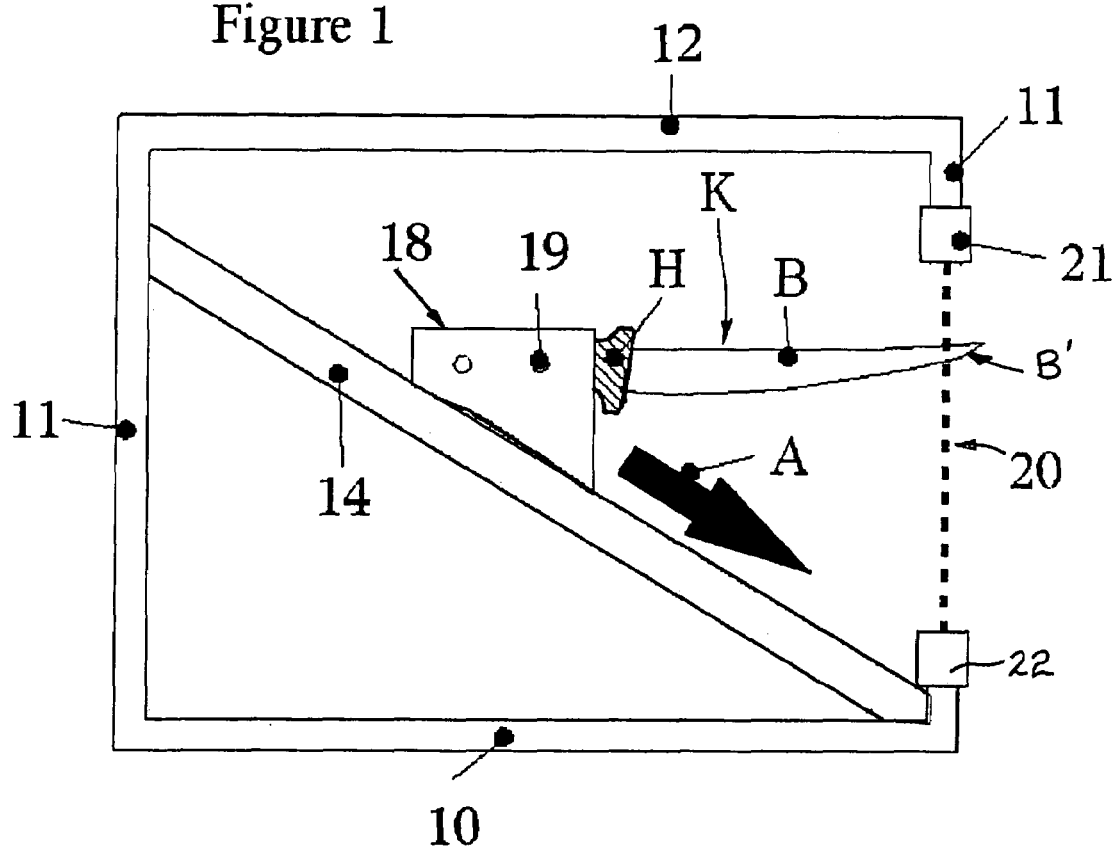
FIG. 1 is a side elevation view of the sharpness tester with a handled knife clamped in the blade holder and the blade performing a cutting action on the material.
Figure 2:
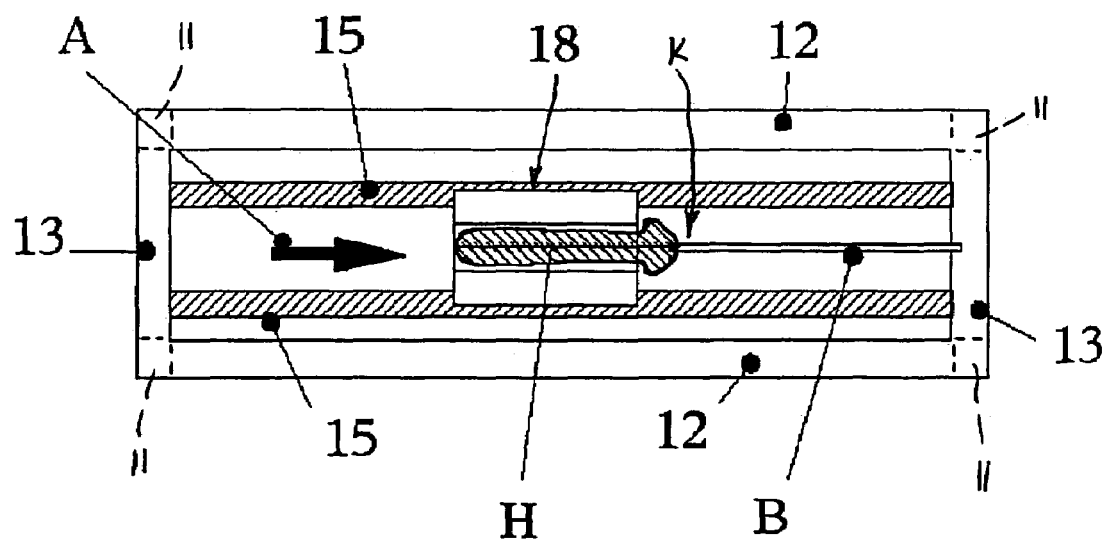
FIG. 2 is an upper perspective view of the sharpness tester as shown in FIG. 1.

In the form of the sharpness tester, which has currently been developed, and as shown in the drawings, there is provided a base 10 with a frame. The frame includes four upwardly extending columns 11 fixed thereto. Longitudinal brace members 12 are provided at the upper ends of the columns while upper cross-bracing members 13 extend laterally.

It will be appreciated by those skilled in the art that the illustrated form of the frame and tracks (hereinafter described) is by way of example only. Many framing and track configurations or methods can be used to achieve a similar effect to that achievable by the described embodiment.

Extending at an incline is a track 14. In the preferred embodiment track 14 is formed by a pair of parallel track members 15. Each of the track members 15 is mounted at an upper end to respective of the laterally opposing columns 11. The lower ends of the track members 15 are anchored either to the base 10 or to lower portions of the other pair of laterally opposed columns 11. In the illustrated form the lower end of the trade member 15 is engaged with a cross piece which extends between the corners formed by the join of the base 10 and columns 11.

A carriage 18 slidingly engages on the track 14. This carriage 18 incorporates or supports a clamp 19. As shown, the handle H of a knife K can be clamped within the clamp 19 so that the blade B of the knife K is forward facing relative to downward movement (see arrow A) of the carriage 18 on the track 14. It will be appreciated that while the tester is primarily intended to test the sharpness of a hand held knife, the blade could equally be a separate item or mounted with some mounting structure other than a handle. For example, the blade could be held (mounted) by a blade mounting, which is intended, in use of the blade, to be installed in a machine or some cutting apparatus.

Any suitable method of clamping the handle H or the blade B itself can be used. The clamp 19 could simply be a pair of clamp plates either both movable or one movable relative to the other. Controlled movement could be either by way of mechanical means or electrical means or hydraulically or pneumatically. The particular manner in which the handle H or blade B is clamped is not part of the present invention. The clamping method used will, however, need to be sufficient i.e. sufficient clamping force to retain the handle H or a blade B in a fixed, stable and immovable position.

The clamp may be designed to enable a variable angle of inclination relative to the inclined tracks 14 and 15. This enables both straight and curved blades to be accurately tested.

Likewise, the means of moving the carriage is not critical to the invention. According to one embodiment of the invention, movement of the carriage 18 can be a means, which enables controlled linear motion e.g. an electrically powered linear actuator 24. It will be appreciated by those skilled in the art that other moving means are useable. These can be hydraulic or pneumatic actuators, a motor drive chain, mechanical means such as toothed rack and pinion to mention but a few of the available options.

Mounted between the base 10 and the cross-member 13, which is located above the lower end of the track 14, is a length of material 20. This length of material 20 can be made from any suitable material including animal tissue. The upper end of the section of material 20 is clamped or otherwise fastened to a force measuring device 21 (e.g. a load cell), which in turn is supported from a support bracket mounted to the cross-member 13. The lower end of the material 20 is anchored by an anchor clamp or the like 22.

As the carriage 18 is moved in a controlled manner down track 14 the distal end B' (or point) of the blade B engages with the material 20. In some embodiments of the present invention the carriage 18 may include a puncturing means (not shown) e.g. a separate blade, which punctures the material 20 prior to the leading part, i.e. distal end B', of the blade B. This will remove the need for the blade to actually puncture the material 20.

As the carriage continues its downward movement the blade B moves through and down the material 20, cutting the material as it does so. Via the force measuring device 21 a signal is generated which is indicative of force. This signal is in turn transmitted via an amplifier 25 and analog to digital converter 26 to and stored in a microprocessor or similar device 27. Accordingly peak analysis and score generation can take place to provide measurement of sharpness.

As the carriage 18 moves downwardly the location of the carriage is recorded by way of a signal being generated by a linear distance measurement device 23 (e.g. a linear potentiometer) and sent to the microprocessor 27. The position of the carriage 18 and hence the extent to which the blade B has progressed through the material 20 is matched with the force as measured by the gauge 21.

Figure 3:
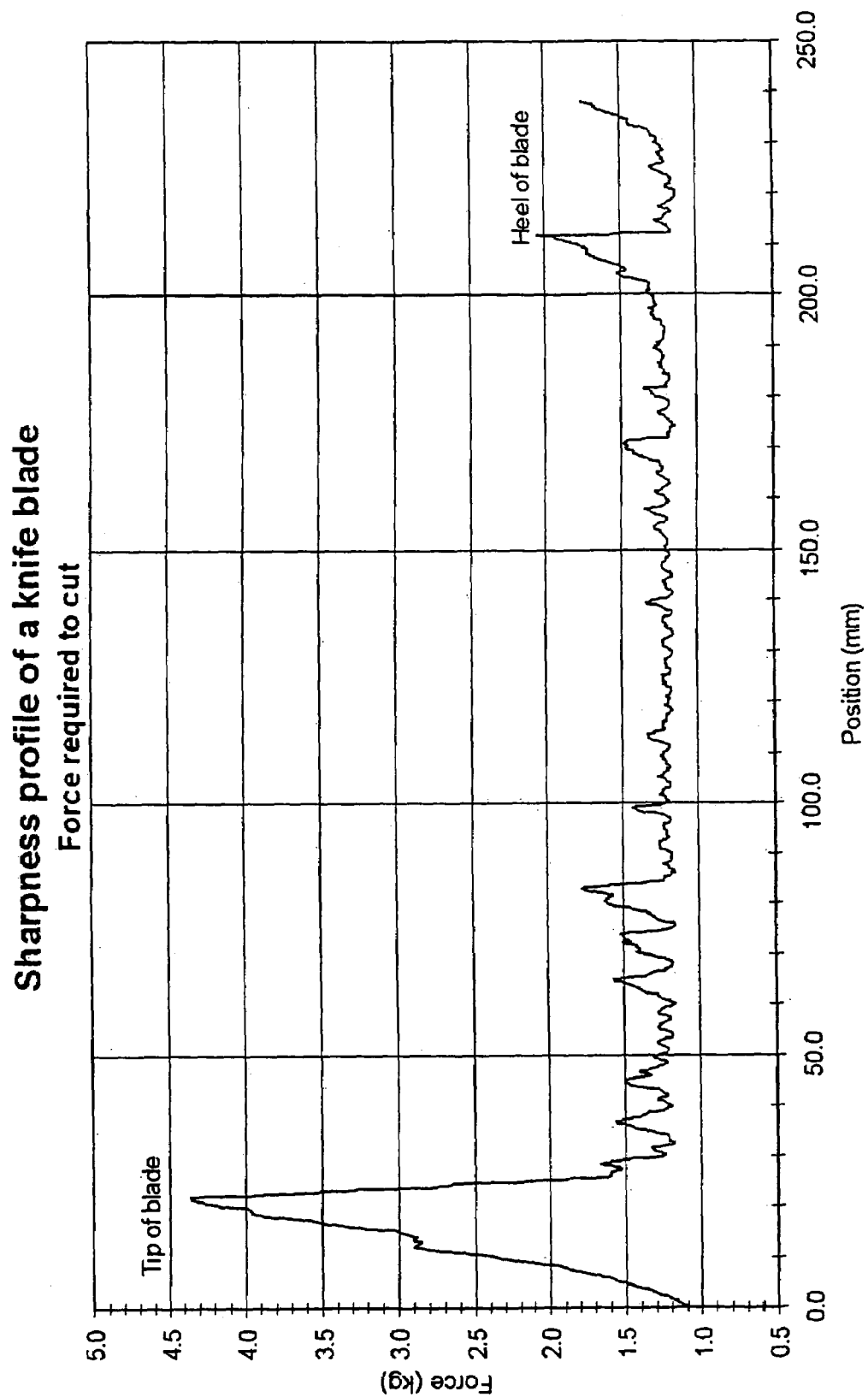
FIG. 3 is a sample plot of a graph showing a plot at distance v force for a blade tested in an embodiment of the sharpness tester according to the invention.
Figure 4:
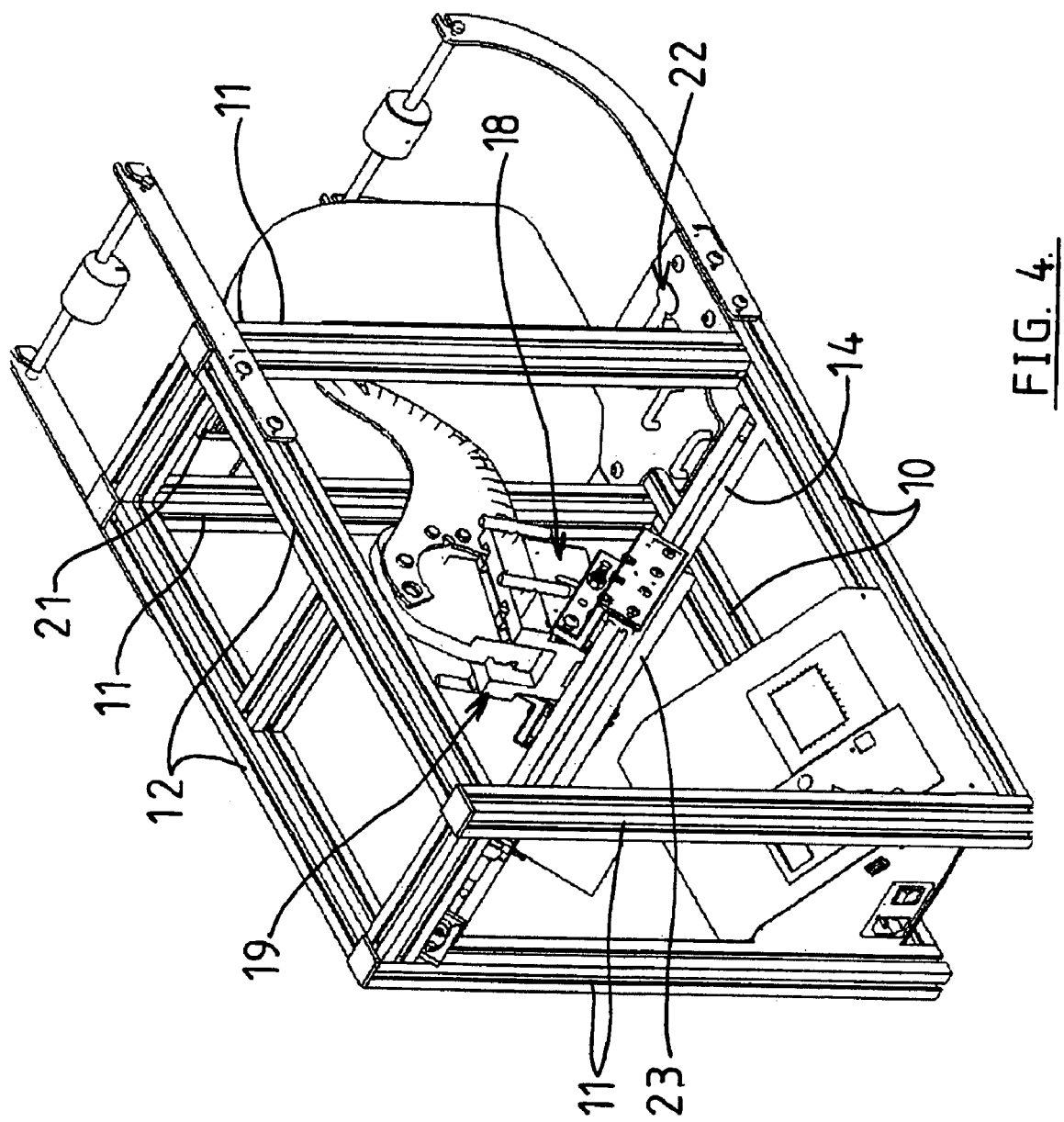
FIG. 4 is an illustration of a commercial form of the invention.
Figure 5:
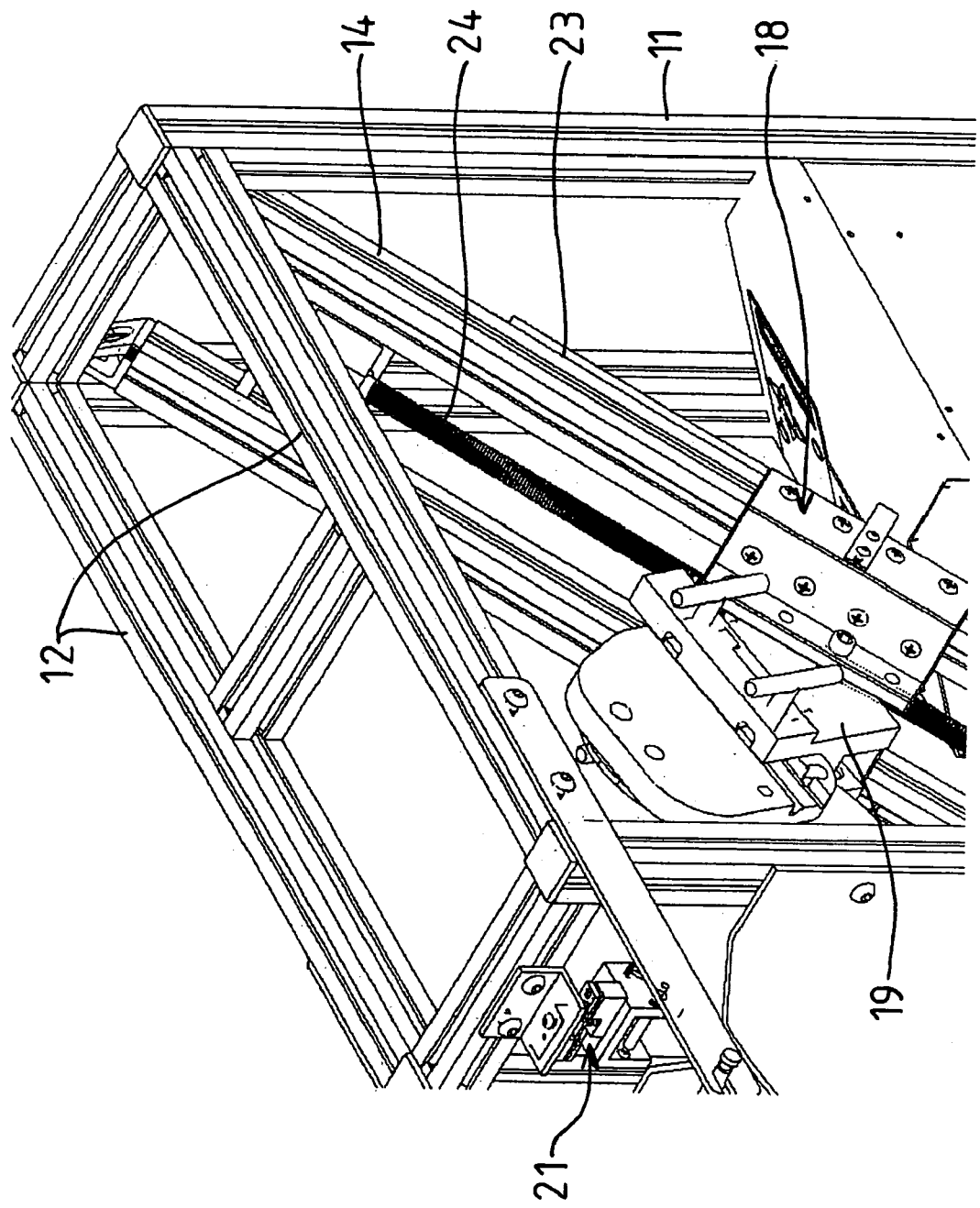
FIG. 5 is a more detailed illustration of the version shown in FIG. 4.
Figure 6:
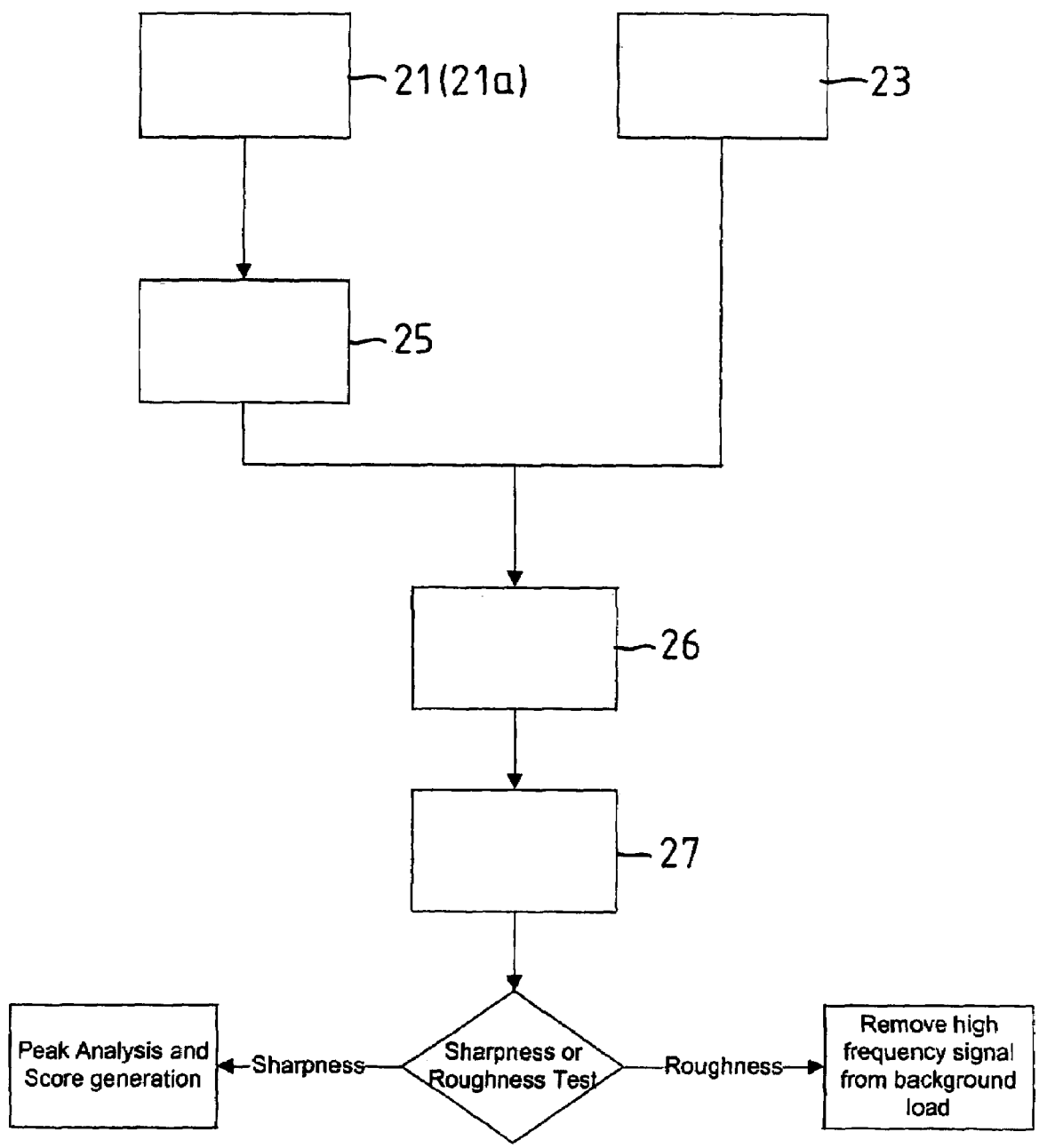
FIG. 6 is a block diagram of the electronic elements of the invention built for sharpness and roughness testing.

The microprocessor 27 can thus generate a profile of the force needed to cut the material at the points along the length of the blade at which readings have been taken. A sample plot of distance versus force is shown in FIG. 3.

The sharpness tester according to the present invention thus measures the ability of a blade to cut by measuring the force required to cut a strand of material. It will be apparent to those skilled in the art that the material could be that, or representative of the, material which the blade will be used, in normal use, to cut. By cutting strands, at different and multiple parts along the blade B, the profile of the cutting ability of the blade along its entire length can be generated. Therefore objective and quantified results can be achieved.

The sharpness tester enables the cutting profile to be obtained with minimal damage to the edge of the blade. Thus the blade can be used after testing.

The apparatus is quick and simple to use and the results are available quickly. This would for example provide instant feedback on sharpening performance. The person sharpening the blade can thus identify a blunt portion or portions of the edge and rectify this by further sharpening.

The invention is open to modification and one such modification is to arrange the tester device so that a measurement of edge roughness of the blade B can be obtained. Such a modification is illustrated in FIG. 7.

According to such modification a strand of non-cuttable material 20*a* (for example wire) is tensioned between a load cell 21*a* and a fixed clamp 22*a*. The clamp 22*a* provides a pre-load on the strand 20*a* prior to testing.

Figure 7:
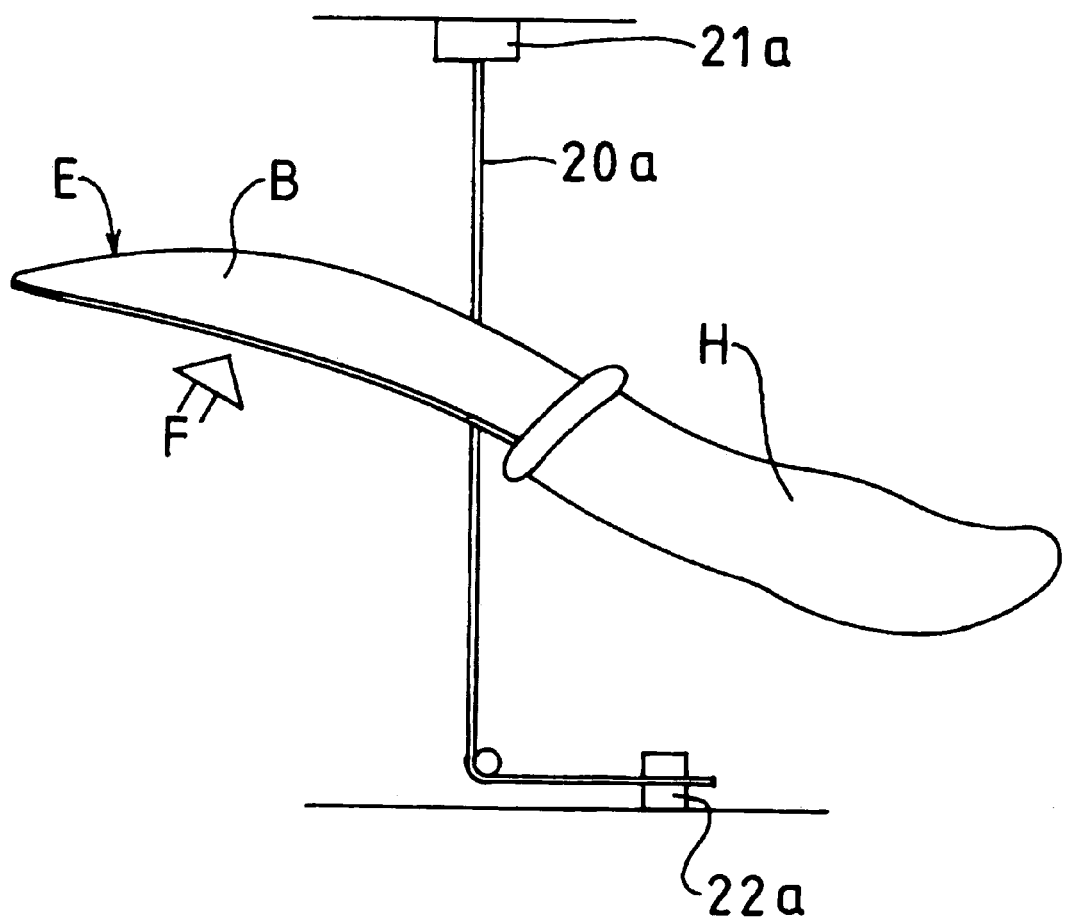
FIG. 7 is a schematic illustration of the sharpness tester when used for roughness testing.

FIG. 7 shows the blade orientation such that the blade B is run across the wire 20*a* with a known applied force or consistent force F applied to the strand 20*a* by the edge E of the blade B. The force F can be manually applied but could be mechanically applied. Force feedback is supplied via readout from the load cell 21*a*.

The variation in tension (signal amplitude) as the blade edge passes across the strand 20*a* is measured via the output of the load cell 21*a*. The output signal of the load cell is amplified by amplifier 25 and passes through analog to digital converter 26 to computer 27 e.g. laptop or PC. The output is then analysed to remove high frequency signal from background load. In this way a measurement of indication of the amplitude variation due to variation in the roughness of the edge of the blade can be achieved. Accordingly, the apparatus can be used to provide a quick and simple means of measuring edge roughness to enable a person sharpening the blade to identify rough portions and take rectifying action.

What is claimed is:

1. A roughness tester, comprising:
   a blade holder,
   a mounting arrangement for mounting of a single strand of non-cuttable material,
   a moving mechanism to cause relative movement between the blade holder and the mounting arrangement, and hence the material when mounted by the mounting arrangement,
   whereby during such relative movement the blade held by the blade holder movably contacts the material, and
   a force measuring device and a location measurement device both operable, in use, to determine variations in the force along the blade as parts of the blade contact the material.

2. A tester as claimed in claim 1 wherein the blade holder is carried by a carriage, which is moveable by the moving mechanism relative to the mounting arrangement.

3. A tester as claimed in claim 2 wherein the carriage is movably mounted on a track, which is inclined relative to the plane of material when the material is retained by the mounting arrangement.

4. A tester as claimed in claim 3 wherein the track is formed by a pair of parallel track members.

5. A tester as claimed in claim 4 wherein the track members are located in a fixed relationship by a frame comprising a base with four spaced apart columns, there being upper and lower cross members which extend between pairs of said columns, the tracks being mounted at the upper and lower ends thereof to the upper and lower cross members.

6. A tester as claimed in claim 2 wherein the blade holder includes clamping means for removable clamping of the blade or some structure with which the blade is mounted.

7. A tester as claimed in claim 2 wherein the moving mechanism is a means for enabling controlled linear motion.

8. A tester as claimed in claim 1 wherein the location measurement device is a linear distance measurement device, operable to generate a signal representative of the position of the blade holder.

9. A tester as claimed in claim 8 wherein the force measuring device forms part of the mounting arrangement.

10. A tester as claimed in claim 9 further including a microprocessor programmed to generate a profile of the force measured, mounted by the mounting arrangement, at points along the length of the blade, the microprocessor programmed to generate the profile from information received from the linear measurement device and force measuring device.

11. A tester as claimed in claim 1, further including a fixed anchoring device, wherein the force measuring device is a load cell and the material is tensioned between the load cell and the fixed anchoring device.

12. A tester as claimed in claim 1 wherein the single strand is a length of wire.

13. A tester as claimed in claim 1 wherein the mounting arrangement is arranged such that the blade is run across the strand with at least initially a known applied force.

14. A tester as claimed in claim 11 further including detection means to detect variations in an output of the load cell and provide a measurement of such variations to indicate roughness of the edge of the blade along at least part of the length thereof.

* * * * *